(12) United States Patent
Beran et al.

(10) Patent No.: US 9,033,900 B1
(45) Date of Patent: May 19, 2015

(54) APPARATUS AND METHOD FOR HEART AND LUNG SOUNDS AUSCULTATION AND TEMPERATURE MEASUREMENTS

(71) Applicants: Anthony V Beran, Yorba Linda, CA (US); Kerry J Tomic-Edgar, Yorba Linda, CA (US)

(72) Inventors: Anthony V Beran, Yorba Linda, CA (US); Kerry J Tomic-Edgar, Yorba Linda, CA (US)

(*) Notice: Subject to any disclaimer, the term of this patent is extended or adjusted under 35 U.S.C. 154(b) by 0 days.

(21) Appl. No.: 13/998,428

(22) Filed: Oct. 30, 2013

(51) Int. Cl.
*A61B 5/00* (2006.01)
*A61B 7/02* (2006.01)

(52) U.S. Cl.
CPC ...................................... *A61B 7/023* (2013.01)

(58) Field of Classification Search
USPC .......................................... 600/549, 559, 586
See application file for complete search history.

(56) References Cited

U.S. PATENT DOCUMENTS

| | | | |
|---|---|---|---|
| 3,951,136 A * | 4/1976 | Wall | 600/380 |
| 4,475,555 A * | 10/1984 | Linder | 600/483 |
| 4,475,559 A * | 10/1984 | Horn | 600/529 |
| 4,517,984 A * | 5/1985 | Perlin | 600/380 |
| 4,724,922 A * | 2/1988 | Kalayjian | 181/135 |
| 4,981,139 A * | 1/1991 | Pfohl | 600/484 |
| 5,010,890 A * | 4/1991 | Pfohl et al. | 600/528 |
| 5,076,284 A * | 12/1991 | Joyce et al. | 600/586 |
| 5,176,150 A * | 1/1993 | Hartwig | 600/586 |
| 6,238,349 B1 * | 5/2001 | Hickey | 600/486 |
| 8,434,487 B2 * | 5/2013 | Nelson et al. | 128/207.15 |
| 2011/0201968 A1* | 8/2011 | Goldstein | 600/586 |
| 2013/0066235 A1* | 3/2013 | Muraco et al. | 600/586 |

* cited by examiner

*Primary Examiner* — Max Hindenburg
(74) *Attorney, Agent, or Firm* — Gray Law Firm; Gordon E. Gray, III

(57) ABSTRACT

The present invention is an esophageal stethoscope with a temperature sensor and earpiece. An esophageal stethoscope has a tube with a first end and a second end, where a sound-transmitting hydrophobic cuff covers the first end of the tube. The first end of the tube has a plurality of lateral openings and a thermistor extending from the first end but within the cuff. The second end of the tube is attached to a connector and has a temperature sensor sub-assembly that extends out of the second end and is connected to the thermistor. A monoscope tube is attached to the connector at a first end and has a memory foam earpiece at a second end. The monoscope tube also preferably has a clip near the earpiece. To facilitate sound transmission, monoscope tubes of different ID sizes are used.

13 Claims, 3 Drawing Sheets

APPARATUS AND METHOD FOR HEART AND LUNG SOUNDS AUSCULTATION AND TEMPERATURE MEASUREMENTS

TECHNICAL FIELD

The present invention is an esophageal stethoscope with a temperature sensor and earpiece.

BACKGROUND ART

Esophageal stethoscopes are used in anesthetized patients and are placed inside the patient's esophagus. Esophageal stethoscopes have been used in clinical applications for continuous measurement of temperature and auscultation of heart and lung sounds.

However, when used, the sound-transmitting portion of the stethoscope is temporarily connected to a separate, custom made connecting line with an earpiece or disposable monoscope. Users often forget or lose the earpiece or monoscope. Consequently, auscultations of heart and lung sounds are often not or cannot be performed. Thus, a complete "ready-to-use" device that incorporates the esophageal stethoscope with temperature sensor portion and monoscope into a single unit is desired. This "ready-to-use" device, because of its ease of application, would greatly improve its clinical usefulness by providing the information needed for optimal patient care.

SUMMARY OF THE INVENTION

The present invention is an esophageal stethoscope with a temperature sensor and earpiece. An esophageal stethoscope has a tube with a first end and a second end, where a sound-transmitting hydrophobic cuff covers the first end of the tube. The first end of the tube has a plurality of lateral openings and a thermistor extending from the first end but within the cuff. The second end of the tube is attached to a connector and has a temperature sensor sub-assembly that extends out of the second end and is connected to the thermistor. A monoscope tube is attached to the connector at a first end and has a memory foam earpiece at a second end. The monoscope tube also preferably has a clip near the earpiece. To facilitate sound transmission, monoscope tubes of different ID sizes are used.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Figure 1:
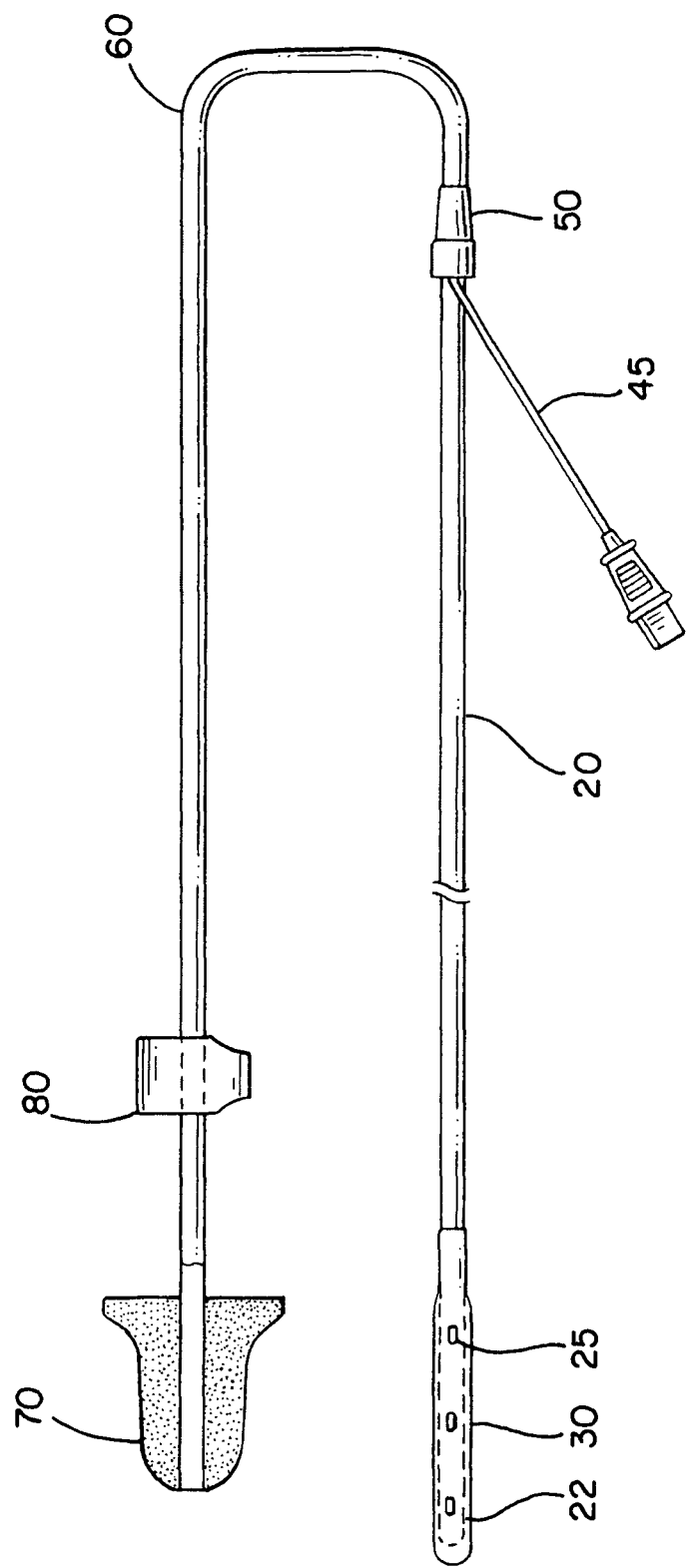
FIG. 1 is a top perspective view of a preferred embodiment of the invention with permanently attached configuration; and, FIG. 2 is a top perspective view of a preferred embodiment of the invention with a disconnected configuration; and, FIG. 3 is a partial cross-sectional view of a preferred embodiment of the invention.

Various embodiments are now described with reference to the drawings, wherein like reference numerals are used to refer to like elements throughout. In the following description, for purposes of explanation, numerous specific details are set forth in order to provide a thorough understanding of one or more embodiments. It may be evident, however, that such embodiment(s) may be practiced without these specific details.

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s). The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide an esophageal stethoscope with a temperature sensor and earpiece.

Figure 3:
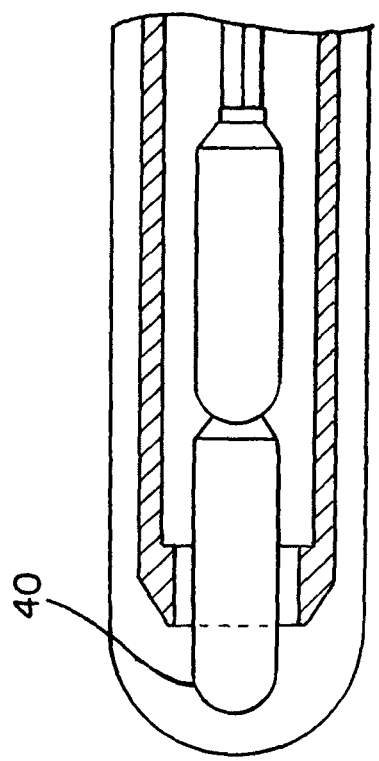

Referring now to FIG. 1, a preferred embodiment of the invention is shown. The esophageal stethoscope 10 preferably has a tube 20 with a first end and a second end. The tube 20 is preferably polyvinyl chloride (PVC). The first end of the tube preferably has a beveled tip 22 and a number of lateral openings 25. The lateral openings are for receiving and transmitting heart and lung sounds for auscultations. The first end of the tube 20 is preferably covered by a cuff 30. The cuff 30 is preferably of sound transmitting quality and it is hydrophobic to resist body fluids entering the stethoscope. A temperature sensor 40, preferably a thermistor, extends through the end of the tube 20, but remains within the cuff 30. The thermistor is preferably a thermistor YSi 400 series equivalent. A close up view of the tip of the tube 20 with the temperature sensor 40 from FIG. 1 is shown in FIG. 3.

Referring back to FIG. 1, the temperature sensor 40 is preferably wired through the length of the tube 20 to a temperature sensor sub-assembly 45 that extends out of the second end of the tube 20. The temperature sensor sub-assembly 45 terminates with an electric connector 46 for an interconnection with an instrument cable. The instrument cable can be connected to a number of different displays for read out of temperature data from the sensor 40.

A connector 50 is preferably affixed to the second end of the tube 20. The connector 50 is preferably a connector that can accept tubing on both ends. In the embodiment shown in FIG. 1, a monoscope tube 60 is permanently attached to the connector 50 at a first end. Thus, FIG. 1 can be referred to as a permanently attached configuration. The monoscope tube 60 is preferably PVC and, in order to facilitate optimal sound transmission, can have different inner diameter (ID) sizes for different esophageal stethoscope sizes. The monoscope tube 60 preferably has an earpiece 70 at a second end. The earpiece 70 is preferably made of memory foam and has a design disclosed by U.S. Pat. Nos. 4,724,922 and 5,002,151, which are incorporated fully herein by reference. The permanently attached monoscope tube 60 and earpiece 70 shown in FIG. 1 prevents a user from losing a separate monoscope or stethoscope attachment and allows a user to more easily conduct auscultations on a patient. The embodiment in FIG. 1 is a preferred embodiment for the needs of a single care provider. Preferably, the monoscope tube 60 has a clip 80, such as a u-type clip. The clip 80 can be used to keep the monoscope tube 60 and earpiece 80 in a desired position or location.

Figure 2:
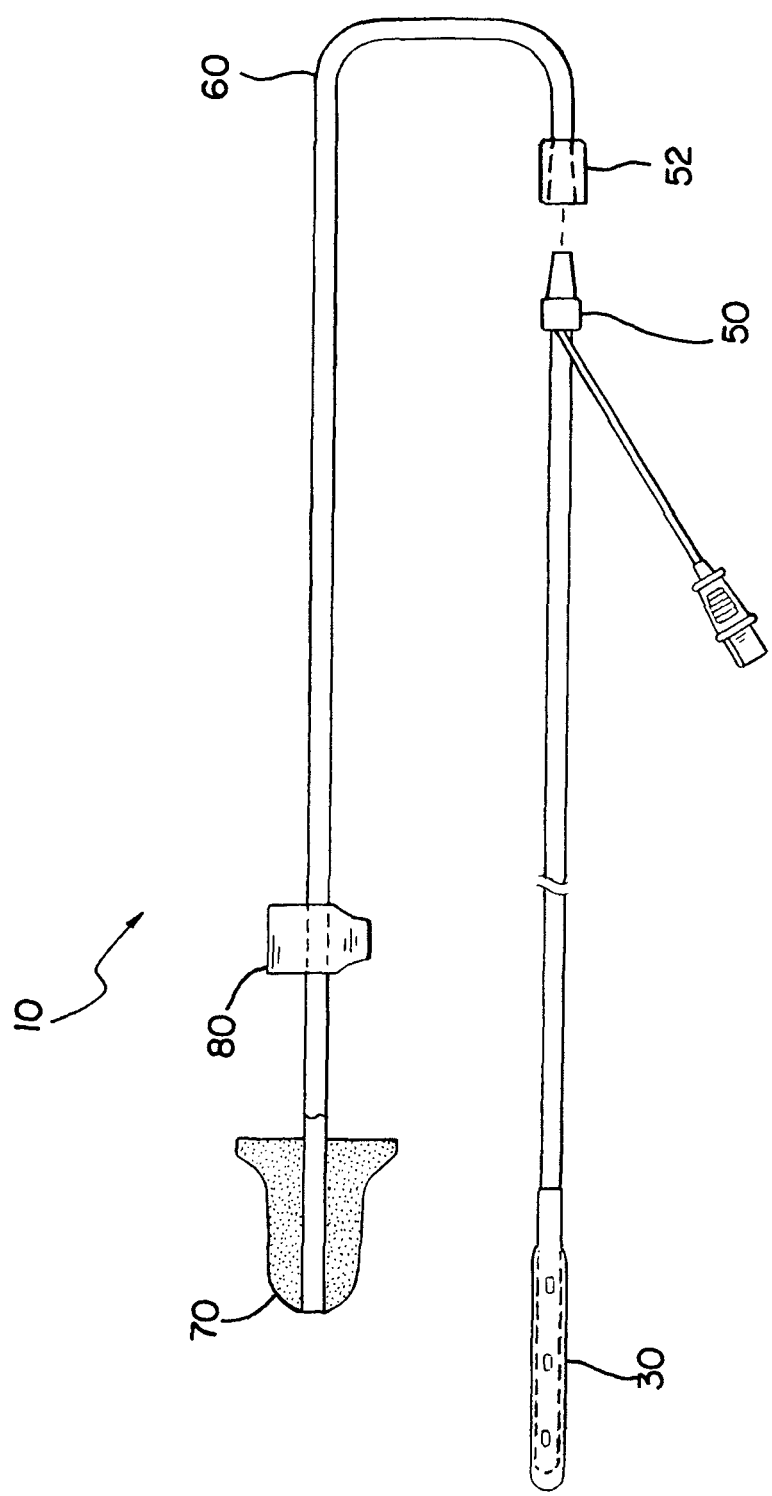

Referring now to FIG. 2, another embodiment is shown where the monoscope 60 can be disconnected from the stethoscope 10. As shown in FIG. 2, a connector 50 is preferably affixed to the second end of tube 20. The connector 50 is preferably a male Luer connector designed to interconnect with a female Luer connector 52. The monoscope tubing 60 is permanently attached to the female Luer connector 52. The monoscope 60 then can, as needed, be connected to the male Luer portion of connector 50. The monoscope tubing 60 is preferable PVC, and in order to provide optimal sound transmission, can have different ID sizes for different esophageal stethoscope sizes. The monoscope tube 60 preferably has an earpiece 70 at the second end. The earpiece 70 is preferably made of memory foam and has a design as described above. The embodiment in FIG. 2 provides for ease of application in particular situations because it has a ready to use form, and allows for an easy disconnection of the monoscope when procedural requirements put the user outside of the reach of the tube 60. With the embodiment in FIG. 2, the user can maintain possession of the earpiece and disconnect at the stethoscope. In addition, the FIG. 2 configuration allows multiple users to use a single stethoscope in place in a patient. The clip 80 is the same as described under 5.

Thus, an improved esophageal stethoscope with a temperature sensor and earpiece is described above. In each of the above embodiments, the different positions and structures of the present invention are described separately in each of the embodiments. However, it is the full intention of the inventor of the present invention that the separate aspects of each embodiment described herein may be combined with the other embodiments described herein. Those skilled in the art will appreciate that adaptations and modifications of the just-described preferred embodiment can be configured without departing from the scope and spirit of the invention. Therefore, it is to be understood that, within the scope of the appended claims, the invention may be practiced other than as specifically described herein.

Various modifications and alterations of the invention will become apparent to those skilled in the art without departing from the spirit and scope of the invention, which is defined by the accompanying claims. It should be noted that steps recited in any method claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

While various embodiments of the present invention have been described above, it should be understood that they have been presented by way of example only, and not of limitation. Likewise, the various diagrams may depict an example architectural or other configuration for the invention, which is done to aid in understanding the features and functionality that may be included in the invention. The invention is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the present invention. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. An esophageal stethoscope comprising:
   a tube with a first end and a second end, where the first end of the tube is covered by a cuff;
   the first end of the tube having a plurality of lateral openings and a temperature sensor within the cuff;
   the second end of the tube is attached to a connector and where a temperature sensor subassembly extends out of the second end and is connected to the temperature sensor; and,
   a monoscope tube is permanently attached to the connector at a first end and has an earpiece at a second end.

2. The esophageal stethoscope of claim 1 where the monoscope tube is chosen from a variety of tubes with different inner diameters for optimal sound modulation.

3. The esophageal stethoscope of claim 1 where the cuff has sound transmitting properties and is hydrophobic.

4. The esophageal stethoscope of claim 1 where the temperature sensor is a thermistor.

5. The esophageal stethoscope of claim 1 where temperature sensor extends beyond the first end of the tube.

6. The esophageal stethoscope of claim 1 further comprising a clip attached to the monoscope tube.

7. The esophageal stethoscope of claim 1 where the earpiece is memory foam.

8. An esophageal stethoscope comprising:
   a tube with a first end and a second end, where the first end of the tube is covered by a sound transmitting and hydrophobic cuff;
   the first end of the tube having a plurality of lateral openings and a thermistor extending from the first end but within the cuff;
   the second end of the tube is attached to a connector and where a temperature sensor sub-assembly extends out of the second end and is connected to the thermistor; and,
   a monoscope tube is permanently attached to the connector at a first end and has a memory foam earpiece at a second end.

9. The esophageal stethoscope of claim 8 further comprising a u-type clip attached to the monoscope tube.

10. The esophageal stethoscope of claim 9 where the monoscope tube is chosen from a variety of tubes with different inner diameters for optimal sound modulation.

11. An esophageal stethoscope comprising:
    a tube with a first end and a second end, where the first end of the tube is covered by a sound transmitting and hydrophobic cuff;
    the first end of the tube having a plurality of lateral openings and a thermistor extending from the first end but within the cuff;
    the second end of the tube is attached to a male Luer connector and where a temperature sensor sub-assembly extends out of the second end and is connected to the thermistor; and,
    a monoscope tube is removably attached to the male luer connector by a female luer connector at a first end and has a memory foam earpiece at a second end.

12. The esophageal stethoscope of claim 11 further comprising a u-type clip attached to the monoscope tube.

13. The esophageal stethoscope of claim 11 where the monoscope tube is chosen from a variety of tubes with different inner diameters for optimal sound modulation.

* * * * *